(12) United States Patent
Badami

(10) Patent No.: US 9,146,266 B2
(45) Date of Patent: Sep. 29, 2015

(54) ACOUSTIC METHODS FOR SENSOR COMMUNICATION

(71) Applicant: General Electric Company, Schenectady, NY (US)

(72) Inventor: Vivek Venugopal Badami, Schenectady, NY (US)

(73) Assignee: General Electric Company, Schenectady, NY (US)

( * ) Notice: Subject to any disclaimer, the term of this patent is extended or adjusted under 35 U.S.C. 154(b) by 302 days.

(21) Appl. No.: 13/687,707

(22) Filed: Nov. 28, 2012

(65) Prior Publication Data

US 2014/0144257 A1   May 29, 2014

(51) Int. Cl.
| | |
|---|---|
| *H04B 11/00* | (2006.01) |
| *G01R 29/02* | (2006.01) |
| *G01N 29/04* | (2006.01) |
| *G01N 29/24* | (2006.01) |
| *G01N 29/34* | (2006.01) |

(52) U.S. Cl.
CPC .............. *G01R 29/02* (2013.01); *G01N 29/043* (2013.01); *G01N 29/2475* (2013.01); *G01N 29/348* (2013.01); *H04B 11/00* (2013.01); *G01N 2291/048* (2013.01); *G01N 2291/106* (2013.01); *G01N 2291/2693* (2013.01); *Y02E 10/722* (2013.01)

(58) Field of Classification Search
CPC ....................................................... H04B 11/00
USPC .................... 73/660; 324/207.25; 340/870.16
See application file for complete search history.

(56) References Cited

U.S. PATENT DOCUMENTS

| | | | |
|---|---|---|---|
| 5,159,580 A | 10/1992 | Andersen et al. | |
| 5,982,297 A | 11/1999 | Welle | |
| 6,127,942 A | 10/2000 | Welle | |
| 6,625,084 B1 | 9/2003 | Payton | |
| 6,717,418 B2 | 4/2004 | Orenstein | |
| 6,891,481 B2 * | 5/2005 | Dubinsky et al. .......... | 340/854.4 |
| 7,782,709 B2 * | 8/2010 | Esmersoy ....................... | 367/31 |

\* cited by examiner

*Primary Examiner* — John Chapman, Jr.
(74) *Attorney, Agent, or Firm* — Ernest G. Cusick; Frank A. Landgraff

(57) ABSTRACT

A system for monitoring equipment and transmitting data and/or signals from one or more satellite nodes to a base node for transmission to a monitor or controller for the equipment. The system may transmit high frequency acoustic signals from one or more satellite nodes embedded in the equipment through a structural component of the equipment to the base node, eliminating the need to hardwire the satellite nodes in harsh environments.

20 Claims, 2 Drawing Sheets

ACOUSTIC METHODS FOR SENSOR COMMUNICATION

TECHNICAL FIELD

The present disclosure relates to methods, systems, and apparatus useful in monitoring and/or controlling various types of equipment.

BACKGROUND

Sensors are typically used in connection with performing monitoring, diagnostics, lifing, and control operations of large pieces of equipment such as gas, steam, and wind turbines, generators, and boilers. Such equipment typically resides in harsh, limited access environments. A major barrier to the wider deployment of new sensors in such environments is the need to install separate power and signal wire conduits for each sensor individually. Signal and power wires are expensive to install in power generation applications, since they must survive for long periods of time in harsh environments, and often must be certified for use in potentially hazardous environments. This increases the cost and therefore the ability to deploy advanced sensing technologies in such environments. Radio frequency based wireless communication solutions are expensive, and not well suited to harsh environments.

SUMMARY

According to the present disclosure, there is provided a method that may comprise sensing, through a sensor attached to a structure comprising a component of a piece of equipment, a signal being transmitted through the structure, transducing, via a transducer connected to the sensor, the sensor signal into an ultrasonic signal, transmitting the ultrasonic signal through the structure to a base node attached to the structure, transducing the ultrasonic signal at the base node into an electrical signal, relaying the electrical signal through a wired connection of the base node to monitoring or control equipment configured to monitor or control the piece of equipment.

According to another aspect of the disclosure, there is provided a system that may comprise a plurality of satellite nodes each comprising a sensor connected to a transducer, each transducer configured to transduce a signal received from the respective sensor to which each transducer is connected into an ultrasonic signal, the satellite nodes being associated with a structure comprising a component of a piece of equipment, a base node associated with the structure and spaced from the satellite nodes, the base node configured to receive ultrasonic signals transmitted from the satellite nodes through the structure and transduce the ultrasonic signals into electrical signals, and a wired connection connected to the base node and configured to relay the electrical signals to a controller of the piece of equipment.

According to yet another aspect of the disclosure, there is provided an apparatus that may comprise a structure comprising a component of a piece of equipment, the structure capable of transmitting sound therethrough, one or more satellite nodes mounted to the structure, each satellite node configured to receive a signal being transmitted through the structure and transduce the signal into an ultrasonic signal, a base node mounted to the structure, the base node configured to receive the ultrasonic signal transmitted by each satellite node through the structure, transduce the ultrasonic signals into electrical signals, and transmit the electrical signals through a wired connection to a controller of the piece of equipment.

These and other features of the present disclosure will become apparent to one of ordinary skill in the art upon review of the following detailed description when taken in conjunction with the drawings and the appended claims.

DETAILED DESCRIPTION OF ILLUSTRATIVE EMBODIMENTS

Figure 1:
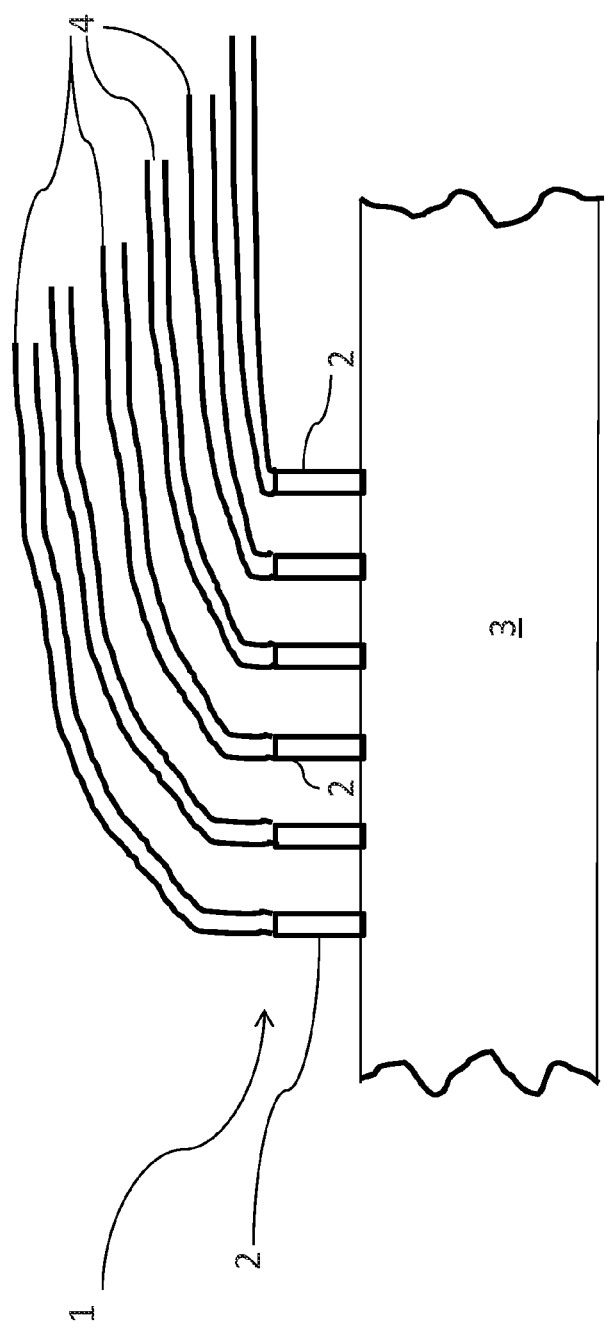
FIG. 1 is an example of a prior art system for monitoring a piece of equipment.

FIG. 1 illustrates a hard-wired monitoring system of the prior art. As illustrated, this system, generally 1, includes a number of wired sensors, 2, each of which is attached to a structure, 3, such as the outer shell of a gas turbine, for example, for monitoring turbine blade health. As illustrated, each sensor 2, has a power and signal wired conduit 4 that may supply power to its associated sensor 2, and transmit information obtained from the sensor 2 to a monitoring and/or control system (not shown).

Figure 2:
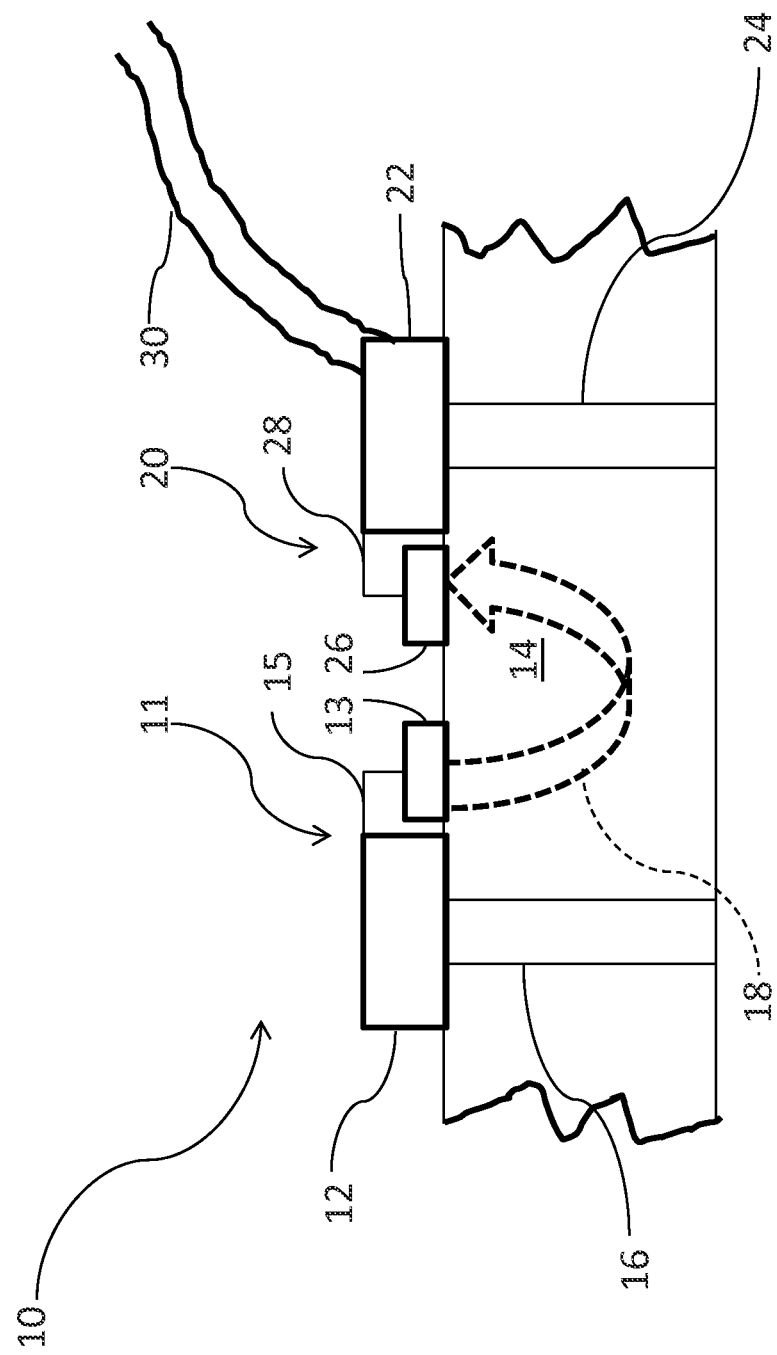
FIG. 2 is a partial cross sectional view of a signal transmitting and monitoring system of the present disclosure.

Referring now to FIG. 2, there is illustrated a monitoring/signal transmitting system of the present disclosure, generally 10. The system 10 may include a satellite node, generally 11, comprising a satellite sensor 12, and a transmitter or transducer 13, associated with a structure 14. The satellite sensor 12 may be a self-powered (energy scavenging) sensor. As illustrated, the satellite sensor 12 may be mounted to the structure 14, and may include a satellite sensor probe 16 that may be embedded in the structure 14. The transmitter 13 may also be mounted to the structure 14, and may be operatively connected to the satellite sensor 12 via a wired connection 15. The satellite sensor may be a passive reluctance or piezoelectric sensor, depending on the application. The satellite sensor 12 may be configured to power its associated satellite transducer 13, preprocess and compress sensor data, and transmit data to the satellite transducer 13.

The structure 14 may comprise a component of a piece of equipment, for example, power generation equipment, such as a component of gas turbines, steam turbines, wind turbines, generators, and boilers that need to be monitored for performance. For example, the structure 14 could be an outer casing for a gas turbine compressor, or the blade of a wind turbine. The structure 14 may be of a material, such as metal or ceramic that is capable of transmitting sound, e.g., acoustic signals, such as ultrasonic signals from one point of the structure 14 through the structure 14 to another point of the structure 14, as illustrated by the dotted arrow 18.

As further illustrated, the acoustic signal 18 may be transduced through the structure 14 via the satellite node transducer 13. The satellite node transducer 13 may be configured to receive a compressed/processed signal and/or data from the satellite sensor 12 through the connection 15, process and/or compress the sensor signal and/or data, and transduce the satellite sensor signal or data into an ultrasonic signal 18. The satellite node transducer 13 may be powered by the satellite sensor 12 to which it is connected, or may be self-powered via energy scavenging. The satellite node transducer 13 may comprise active or passive elements, depending on the application. The satellite node transducer 13 may further be configured to transmit data, such as compressed data and/or an ultrasonic signal, through the structure 14 to a base node, generally 20, which shall now be described.

As illustrated in FIG. 2, the system 10 may further include a base node, generally 20, spaced a distance from the satellite node 11. The base node 20 may also include a base node sensor 22 that may be associated with the structure 14 in a manner similar to the satellite node sensor 12, for example, by being attached thereto or being embedded in the structure 14 with a base sensor probe 24. The base node 20 may further include a base node receiver 26 that may be attached to the structure 20 and operatively connected to the base node sensor 22 via a base node connection 28. The base node sensor 22 may also be self-powered, for example via energy scavenging, and may power the base node receiver 26.

The base node receiver 26 may be configured to receive signals from the base node sensor 22, but may also be configured to receive data and/or signals, such as acoustic signals, for example ultrasonic signals 18 from the satellite node transducer 13. The base node receiver 26 may be powered by the base node sensor 22, or may be self-powered via energy scavenging. The base node receiver 26 may be active or passive, depending on the application. The base node receiver 26 may also be configured to aggregate and transmit all the signals and/or data it receives, and transmit those signals and/or data through a single wired connection 30 to a monitor or controller (not shown) that may be configured to monitor and/or control the performance and operation of the piece of equipment of which the structure 14 is a component. It will be understood that a wireless connection may be used in addition to or in lieu of the wired connection 30.

In one embodiment of the disclosure, a plurality of satellite nodes 11 may be attached to or embedded in the structure 14 in order to monitor different regions of the piece of equipment of which the structure 14 is a component. Each satellite node may transmit, through its respective satellite node transducer 13, signals and/or data through the structure to the base node receiver 26, where the signals and/or data may be aggregated for transmission by the base node sensor 22 to a monitor or controller (not shown), which may act upon the signals or data received to monitor or control the piece of equipment to which the satellite nodes 11 and base node 20 are attached or embedded.

As previously discussed, the structure 14 to which the satellite nodes 11 and base node 20 are attached or embedded may be a component of a larger piece of equipment, such as a gas turbine, steam turbine, wind turbine, generator, or boiler. Such equipment in operation typically produces noise that could interfere with the acoustic transmissions 18 of the system if such noise is not accounted for. One approach to account for such background noise is to transmit the acoustic transmissions 18 at a frequency that is outside the normal spectral range of frequencies of background noise produced by the piece of equipment during normal operation thereof. For example, the transmission 18 may be made at a frequency that is higher than the range of background noise. Alternatively, the background noise of the equipment might be cancelled using noise cancellation techniques known in the art.

In one exemplary system of the present disclosure, the satellite sensor 12 may be a reluctance probe, the structure 14 may be a component of a piece of equipment selected from the group comprising gas turbines and steam turbines, the signal picked up by the reluctance probe may be a voltage pulse from a turbine blade passage, and the satellite node transducers 13 may be piezoelectric transducers. In one such system, the reluctance probe may be used to detect a voltage pulse generated by a passing blade in a gas turbine to provide a blade tip timing signal that is used to derive the vibratory components of the blade for health monitoring. The reluctance probe may also possibly monitor the blade for thermal growth and consequent lessening of clearance between the blade tips and the turbine casing, which can lead to the blade tip contacting the casing, shortening blade life and negatively impacting turbine performance.

In another aspect of the disclosure, each of the satellite node transducers 13 may be configured to encode their respective transduced ultrasonic frequencies into a frequency unique to that satellite node transducer 13, thereby allowing the base node 20 to identify each satellite node and map discrete information obtained from each satellite sensor 12 to that satellite sensor 12 and therefore to the region of the structure 14 to which that satellite sensor 12 is attached or embedded.

This written description uses examples to disclose the invention, including the best mode, and also to enable any person of ordinary skill in the art to practice the invention, including making and using any devices or systems and performing any incorporated methods. The steps recited in the accompanying method claims need not be taken in the recited order, where other orders of conducting the steps to achieve the desired result would be readily apparent to those of ordinary skill in the art. The patentable scope of the invention is defined by the claims, and may include other examples that occur to those of ordinary skill in the art. Such other examples are intended to be within the scope of the claims if they have structural elements that do not differ from the literal language of the claims or if they include equivalent structural elements with insubstantial differences from the literal languages of the claims.

I claim:

1. A method comprising:
    sensing; through a sensor and sensor probe attached to a structure comprising a component of a piece of power generation equipment, a condition of said structure and generating a sensor signal;
    transducing, via a transducer connected to said sensor and sensor probe, the sensor signal into an ultrasonic signal;
    transmitting said ultrasonic signal through said structure to a base node attached to said structure the base node comprising a base node receiver operatively connected to a base node sensor;
    transducing said ultrasonic signal at said base node into an electrical signal;
    relaying the electrical signal through a connection of said base node to monitor or control equipment configured to monitor or control said piece of power generation equipment.

2. The method of claim 1 wherein there is a plurality of said transducers and a plurality of said sensors, each sensor being operatively connected to one of said plurality of said transducers to form a satellite node, and wherein said plurality of said sensors are attached to said structure.

3. The method of claim 2 wherein said plurality of said sensors are embedded in said structure.

4. The method of claim 1 wherein said structure is a component of a piece of power generation equipment selected from the group consisting of gas turbines, steam turbines, wind turbines, generators, and boilers.

5. The method of claim 4 wherein said ultrasonic signal is transmitted at a transmitted frequency outside a normal spectral range of frequencies of background noise produced by said piece of power generation equipment during normal operation thereof.

6. The method of claim 5 wherein said transmitted frequency is higher than said normal spectral range of frequencies of background noise.

7. A method comprising:
sensing through a sensor and sensor probe attached to a structure comprising a component of a piece of power generation equipment, a a condition of said structure and generating a sensor signal;
transducing, via a transducer connected to said sensor and sensor probe, the sensor signal into an ultrasonic signal;
transmitting said ultrasonic signal through said structure to a base node attached to said structure, the base node comprising a base node receiver operatively connected to a base node sensor;
transducing said ultrasonic signal at said base node into an electrical signal; relaying the electrical signal through a connection of said base node to monitor or control equipment configured to monitor or control said piece of power generation equipment;
wherein said sensor is a reluctance probe, said structure is a component of a piece of power generation equipment selected from the group consisting of gas turbines, steam turbines, and wind turbines, said sensor signal is a voltage pulse from a turbine blade passage sensed by said reluctance probe, and said transducer is a piezoelectric transducer.

8. The method of claim 2 wherein each said transducer of said sensor is configured to encode a transduced ultrasonic frequency into a frequency unique to each said transducer, thereby allowing said base node to identify each satellite node.

9. A system comprising:
a plurality of satellite nodes each comprising a sensor and sensor probe connected to a transducer, each transducer configured to transduce a signal, where the signal is received from the respective sensor to which each transducer is connected, into an ultrasonic signal, said plurality of satellite nodes being associated with a structure comprising a component of a piece of power generation equipment;
a base node associated with said structure and spaced from said plurality of satellite nodes, the base node comprising a base node receiver operatively connected to a base node sensor, said base node receiver configured to receive ultrasonic signals transmitted from said plurality of satellite nodes through said structure and transduce said ultrasonic signals into electrical signals; and
a connection connected to said base node and configured to relay said electrical signals to a monitor or controller of said piece of power generation equipment.

10. The system of claim 9 wherein each said sensor is embedded in said structure.

11. The system of claim 9 wherein said piece of power generation equipment is selected from the group consisting of gas turbines, steam turbines, wind turbines, generators, and boilers.

12. The system of claim 9 wherein said ultrasonic signals are transmitted from said plurality of satellite nodes at frequencies that are outside a normal spectral range of frequencies of background noise produced by said piece of power generation equipment during normal operation thereof.

13. The system of claim 9 wherein said sensors are self-powered.

14. The system of claim 9 wherein each said transducer of each said satellite node is powered by the respective sensor to which each said transducer is connected.

15. The system of claim 9 wherein said base node is configured to aggregate the signals received from each said plurality of satellite nodes into aggregated signals and transmit said aggregated signals through said connection to said controller.

16. The system of claim 9 wherein each said sensor is configured to preprocess and compress the signal received from the respective sensor into a compressed signal and transmit the compressed signal to the transducer to which each said sensor is connected.

17. An apparatus comprising:
a structure comprising a component of a piece of power generation equipment, said structure fabricated of a material capable of transmitting sound through said structure;
one or more satellite nodes mounted to said structure, each of said one or more satellite nodes comprising a sensor and sensor probe, and configured to generate a signal responsive to a condition of said structure and transduce said signal into an ultrasonic signal via a transducer connected to said sensor and sensor probe;
a base node mounted to said structure, the base node comprising a base node receiver operatively connected to a base node sensor; said base node configured to receive the ultrasonic signal transmitted by each said one or more satellite nodes through said structure, transduce said ultrasonic signal into electrical signals, and transmit said electrical signals through a connection to a monitor or controller of said piece of power generation equipment.

18. The apparatus of claim 17 wherein said piece of power generation equipment is selected from the group consisting of gas turbines, steam turbines, wind turbines, generators, and boilers.

19. The apparatus of claim 17 wherein each said one or more satellite nodes comprises a reluctance probe, said structure is a component of a piece of power generation equipment selected from the group consisting of gas turbines and steam turbines, said signal received by said one or more satellite nodes is a voltage pulse from a turbine blade passage, and each said one or more satellite nodes comprises a piezoelectric transducer.

20. The apparatus of claim 17 wherein one or more of said satellite nodes are self-powered.

* * * * *